US010376628B2

(12) United States Patent
Blasek et al.

(10) Patent No.: US 10,376,628 B2
(45) Date of Patent: Aug. 13, 2019

(54) METHOD FOR REMOVING FLUID FROM A BLOOD FILTER AT THE END OF A BLOOD TREATMENT SESSION AND TREATMENT APPARATUS FOR EXECUTING THE METHOD

(75) Inventors: Marco Blasek, Niederwern (DE); Joachim Noack, Bad Neustadt (DE)

(73) Assignee: Fresnius Medical Care Deutschland GmbH, Bad Homburg (DE)

( * ) Notice: Subject to any disclaimer, the term of this patent is extended or adjusted under 35 U.S.C. 154(b) by 1010 days.

(21) Appl. No.: 13/559,921

(22) Filed: Jul. 27, 2012

(65) Prior Publication Data

US 2013/0025697 A1    Jan. 31, 2013

Related U.S. Application Data

(60) Provisional application No. 61/512,929, filed on Jul. 29, 2011.

(30) Foreign Application Priority Data

Jul. 29, 2011   (DE) .................. 10 2011 108 785

(51) Int. Cl.
*A61M 1/16*   (2006.01)
*A61M 1/36*   (2006.01)
*A61M 1/34*   (2006.01)

(52) U.S. Cl.
CPC ............ *A61M 1/3643* (2013.01); *A61M 1/16* (2013.01); *A61M 1/1682* (2014.02);
(Continued)

(58) Field of Classification Search
None
See application file for complete search history.

(56) References Cited

U.S. PATENT DOCUMENTS 4,444,597 A * 4/1984 Gortz ................... A61M 1/168
                                                     134/18
2003/0100857 A1* 5/2003 Pedrazzi ............. A61M 1/3643
                                                     604/4.01
(Continued)

FOREIGN PATENT DOCUMENTS

DE   102006012087 A1   9/2007
DE   102009008346 A1   8/2010
WO   1996-40313 A1    12/1996

OTHER PUBLICATIONS

Title:The Solubility of Nitrogen and Air in Liquids Author: Battino Date: 1984 Publisher/Edition: J.Phys.Chem. Ref. Data, vol. 13, No. 2, 1984.*

(Continued)

*Primary Examiner* — Jonathan M Peo
(74) *Attorney, Agent, or Firm* — Fish & Richardson P.C.

(57) ABSTRACT

The present invention relates to a method for removing fluid from a blood filter which is used for the blood treatment of a patient and/or for removing blood from an extracorporeal blood circuit at the end of a blood treatment session. It further relates to a medical treatment apparatus with a control and/or regulating device which executes the method according to the present invention. It further relates to a digital storage medium, a computer program product as well as a computer program for executing the method according to the present invention.

24 Claims, 1 Drawing Sheet

(52) U.S. Cl.
CPC ........ *A61M 1/3465* (2014.02); *A61M 1/3644* (2014.02); *A61M 1/3646* (2014.02); *A61M 1/3649* (2014.02); *A61M 1/3652* (2014.02); *A61M 2205/3331* (2013.01); *A61M 2205/50* (2013.01); *Y10T 137/0419* (2015.04); *Y10T 137/0424* (2015.04)

(56) References Cited

U.S. PATENT DOCUMENTS

| | | | | |
|---|---|---|---|---|
| 2005/0131332 | A1* | 6/2005 | Kelly | A61M 1/1696 604/4.01 |
| 2009/0095679 | A1* | 4/2009 | Demers | A61M 1/16 210/646 |
| 2010/0168640 | A1* | 7/2010 | Kopperschmidt et al. | 604/6.09 |
| 2010/0192686 | A1* | 8/2010 | Kamen | A61M 1/16 73/290 R |

OTHER PUBLICATIONS

Asano et al., "Wastewater Reclamation and Reuse", Water Quality Management Library, vol. 10, published by CRC Press, New York, 1998, p. 267, 4 total pages.*

* cited by examiner

METHOD FOR REMOVING FLUID FROM A BLOOD FILTER AT THE END OF A BLOOD TREATMENT SESSION AND TREATMENT APPARATUS FOR EXECUTING THE METHOD

CROSS REFERENCE TO RELATED APPLICATIONS

This application claims the benefit of U.S. Provisional Patent Application No. 61/512,929 filed on Jul. 29, 2011 and German Patent Application No. 10 2011 108 785.4, filed Jul. 29, 2011, both of which are herein incorporated by reference in their entireties.

FIELD OF INVENTION

The present invention relates to a method for removing fluid from a blood filter for the extracorporeal blood treatment of a patient at the end of the blood treatment session. It further relates to a control device, a medical treatment apparatus, and a computer program for executing the method according to the present invention.

BACKGROUND OF INVENTION

Blood filters and extracorporeal blood circuits are usually disposables and are disposed of after their use. Disposal is cost-intensive and is paid for by weight of waste. For this reason, and also in order to reduce the risk of contamination, these disposables are thus emptied of fluid, and in particular, of blood, before being disposed of It is an object of the present invention to specify a further method as well as a suitable apparatus for removing fluid from a blood filter or a dialysate chamber hereof and optionally from an extracorporeal blood circuit connected herewith.

Thus, according to the present invention, a method for removing fluid from a blood filter used for the blood treatment of a patient at the end of the blood treatment session is proposed. The blood filter comprises a blood chamber and a dialysate chamber between which a membrane is arranged, wherein the blood chamber is connected for the blood treatment with an arterial blood line which leads to the blood chamber and a venous blood line which leads away from the blood chamber as well as a dialysate inlet line which leads to the dialysate chamber and a dialysate outlet line which leads away from the dialysate chamber. The method according to the present invention encompasses displacing the fluid from the dialysate chamber by actively or passively introducing air or a liquid into the dialysate inlet line.

The control device according to the present invention, which may also be embodied as a regulating device, is suitable and provided and/or designed and/or configured for executing the method according to the present invention. It can optionally comprise further devices such as, for example, storage devices, addition devices, automated signaling devices and so on.

The medical treatment apparatus according to the present invention (hereafter also in short: treatment apparatus) comprises at least one extracorporeal blood circuit with a line having interior portion(s). It is further furnished with at least one blood pump for conveying blood within line interior portions of the extracorporeal blood circuit, the blood pump being arranged at or in the extracorporeal blood circuit. In addition, it comprises at least one device, provided for introducing air into a dialysate inlet line which is provided for supplying dialysate to the dialysate chamber of the blood filter during the treatment.

A digital storage medium according to the present invention, in particular in the form of a disk, CD or DVD, USB-Stick, Flashcard, a SD Card, EPROM and the like with electronically readable control signals may interact with a programmable computer system such that the mechanical steps of the method according to the present invention are prompted.

In doing so, all or some of the steps of the method according to the present invention which are executed by the machine may be prompted.

A computer program product according to the present invention comprises a program code saved on a machine-readable storage device for prompting the steps of the method according to the present invention which are executed by the machine when the computer program product runs on a computer.

The term "machine-readable storage device," as used herein, denotes in certain embodiments of the present invention a storage device which contains data or information which is interpretable by software and/or hardware. The storage device may be a data storage device such as a disk, a CD, DVD, a USB stick, a flashcard, an SD card or EPROM and the like.

A computer program according to the present invention comprises a program code for prompting the steps of the method according to the present invention that are carried or out executed by the machine when the computer program runs on a computer.

A digital, particularly a non-volatile storage medium according to the present invention, particularly in the form of a machine-readable data storage device, particularly in the form of a disk, CD, DVD or EPROM, particularly with electronically or optically readable control signals, may interact with a programmable computer system such that the mechanical steps of a method according to the present invention are prompted.

Hereby, all, several or some of the mechanically executed steps of the method according to the present invention may be prompted.

According to the present invention a "computer program product" can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

A "machine-readable data storage device" denotes in certain embodiments of the present invention a medium that contains data or information which is interpretable by software and/or hardware. The medium may be a disk, a CD, DVD, a USB stick, a flash card, an SD card or the like.

A "computer program" according to the present invention can be understood as, for example, a physical software product, which is ready for distribution and contains a computer program.

It also applies for the computer program product according to the present invention and the computer program according to the present invention that all or some of the steps of the method according to the present invention that are executed by the machine are prompted.

In all of the following embodiments, the use of the expression "may be" or "may have" and so on, is to be understood synonymously with "preferably is" or "preferably has," respectively, and so on, and is intended to illustrate an embodiment according to the present invention.

Advantageous developments of the present invention are each subject of dependent claims and embodiments.

Embodiments according to the present invention may comprise one or more of the features named hereafter.

In some embodiments according to the present invention, the method serves to partially, in others to completely remove fluid from a blood filter used for the blood treatment of a patient and/or from the blood circuit after termination of the blood treatment session.

The utilized blood filter is in some embodiments according to the present invention a hemodialyzer.

The membrane arranged between the blood chamber and the dialysate chamber is in certain embodiments according to the present invention a semi-permeable membrane.

In certain embodiments according to the present invention, the venous blood line leads from the blood chamber to a venous connection point.

In some embodiments according to the present invention, instead of air gas or a different gaseous mixture is used or, in particular, introduced into the dialysate inlet line. In some embodiments, air or a liquid is introduced into the dialysate inlet line and/or into the dialysate chamber.

In certain embodiments according to the present invention, the method encompasses regulating or controlling the introduction of air wherein pressure measurements measured by utilization of at least one pressure sensor provided in or on the dialysate inlet line or in or on the dialysate outlet line are taken into account.

In some embodiments according to the present invention, the at least one pressure sensor provided in or on the dialysate outlet line measures a dialysate pressure directly, in others indirectly.

The method encompasses in certain embodiments according to the present invention sealing or closing the arterial blood line and/or the venous blood line against the atmosphere or ensuring such sealing or closure.

In certain embodiments of the method according to the present invention, at least one patient clamp is closed to stop a flow of blood within the arterial blood line and/or the venous blood line. In some embodiments, a single-needle valve is additionally closed.

In some embodiments of the method according to the present invention, an arterial blood line is not connected with a venous blood line for the purpose of emptying the blood filter. In certain embodiments according to the present invention, a connection between the arterial blood line and the venous blood line remains completely undone or is not established.

In certain embodiments according to the present invention, the connection between the arterial blood line and the venous blood line is established, in particular exclusively for the purpose of emptying the blood filter.

In some embodiments according to the present invention, the method encompasses determining or setting or ensuring a pressure in the blood chamber above a dialysate pressure of the dialysate chamber, in particular during any point of time of the emptying process.

In certain embodiments according to the present invention, the method takes place without also emptying the blood chamber of fluid, or without emptying the blood chamber at the same time.

In doing so, the method may proceed such that advantageously no fluid is transferred across the membrane.

In certain embodiments of the method according to the present invention, emptying the dialysate chamber takes place before or simultaneously with emptying the blood chamber or the blood circuit. In some embodiments according to the present invention, emptying the dialysate chamber is finished before emptying the blood chamber or the blood circuit is started.

In some embodiments, emptying the dialysate chamber simultaneously with emptying the blood chamber or the blood circuit means a temporal overlap. In some embodiments according to the present invention, simultaneousness means simultaneous beginning and/or simultaneous ending.

In certain embodiments of the method according to the present invention, blood is removed from the blood filter and/or from an extracorporeal blood circuit which is connected with the blood filter, the extracorporeal blood circuit comprising a line having interior portion(s). This takes place by utilizing at least one blood pump of the treatment apparatus for conveying blood within line interior portions of the extracorporeal blood circuit as well as at least one second conveying device for introducing at least one substituate liquid into line interior portions of the extracorporeal blood circuit and/or conveying the line content within line interior portions of the extracorporeal blood circuit. This encompasses entering air into line interior portions of the extracorporeal blood circuit by operating the blood pump as well as introducing substituate liquid into line interior portions of the extracorporeal blood circuit by operating the second conveying device.

In some embodiments of the method according to the present invention, the method encompasses detecting a qualitative change of the content of line interior portions of the extracorporeal blood circuit.

In certain embodiments of the method according to the present invention, the method encompasses disconnecting the extracorporeal blood circuit from the vascular system of the patient.

In some embodiments according to the present invention of the method, the blood pump conveys a defined volume of air.

In certain embodiments of the method according to the present invention, an air-blood content is conveyed in line interior portions of the extracorporeal blood circuit until an air-blood limit or air-blood boundary or transition reaches an addition point of the extracorporeal blood circuit for substituate liquid into line interior portions of the extracorporeal blood circuit. Furthermore, when the addition point is reached, a substituate liquid is introduced into line interior portions of the extracorporeal blood circuit via the addition point.

In some embodiments of the method according to the present invention, a predetermined amount of substituate liquid is introduced into line interior portions of the extracorporeal blood circuit by operating the conveying device.

In certain embodiments of the method according to the present invention, the substituate liquid is conveyed until the detection device detects substituate liquid in line interior portions of the extracorporeal blood circuit.

In some embodiments of the method according to the present invention, the air-substituate liquid-blood content is conveyed along line interior portions of the extracorporeal blood circuit by operating the blood pump and/or by operating the conveying device.

In certain embodiments of the method according to the present invention, at at least one first point of time substituate liquid is introduced into line interior portions of the extracorporeal blood circuit by utilization of the conveying device, and at at least one second point of time which chronologically differs from the first point of time air is introduced into line interior portions of the extracorporeal blood circuit by utilization of the conveying device.

In some embodiments of the method according to the present invention, the detection device is arranged with a predetermined distance to the second access device. In these embodiments the method further encompasses conveying the content of line interior portions of the extracorporeal blood circuit across or along the predetermined distance to the access device after air has been detected at or by the detection device.

In certain embodiments of the method according to the present invention, blood contained in line interior portions of the extracorporeal blood circuit is inserted into the vascular system of the patient via the second access device.

In some embodiments according to the present invention, the treatment apparatus encompasses at least one detection device which is arranged in a section of the extracorporeal blood circuit for detecting at least one change of the content or one change of a property of the content of line interior portions of the extracorporeal blood circuit.

In some embodiments according to the present invention, the treatment apparatus encompasses at least one conveying device for introducing or inserting at least a substituate liquid into line interior portions of the extracorporeal blood circuit and/or for conveying a line content within line interior portions of the extracorporeal blood circuit.

In some embodiments according to the present invention the method further encompasses inserting, entering or introducing air and substituate liquid into the extracorporeal blood circuit, for example after termination of a blood treatment session.

Such a blood treatment session may be, for example, a treatment unit using hemodialysis, hemofiltration, hemodiafiltration and/or a cell separation method and directed to the treatment and/or purification of blood. For performing such a blood treatment, a suitable blood treatment apparatus is used.

A blood treatment apparatus which is suitable for executing the method according to the present invention comprises in some embodiments according to the present invention an extracorporeal blood circuit having line interior portions or is connected therewith, various conveying devices for introducing and/or conveying various fluids in line interior portions of the extracorporeal blood circuit, and for example a device for treating the blood of the patient, such as one or several blood filters and/or one or several dialyzers and/or one or several adsorbers. It may further comprise containers for storing fluids, elements for introducing the fluids, such as for example tube elements and/or valves, as well as further devices such as for example an air separation chamber or bubble trap for removing air from the blood during the blood treatment and/or sensors and/or detectors for detecting various relevant parameters, such as, for example, a pressure in the extracorporeal blood circuit.

Conveying devices include membrane pumps, tube pumps, roller pumps and so on. The blood pump may be embodied, e.g., as a tube pump or a roller pump.

A peristaltic pump, e.g., a roller pump may be used as conveying device for introducing at least a substituate liquid into line interior portions of the extracorporeal blood circuit and/or conveying a line content within line interior portions of the extracorporeal blood circuit. However, also a different type of pump, e.g., a membrane pump, in particular a highly precisely metering membrane pump, may be used.

This conveying device may be a second conveying device, i.e. a conveying device which is different from the blood pump. The blood pump may, however, also be designed such that it fulfils both the function which is typical for a blood pump and the function of introducing substituate liquid into line interior portions of the extracorporeal blood circuit and/or conveying line content. Whenever a second conveying device is mentioned hereafter just for the purpose of better legibility, this relates to the blood pump or a conveying device which differs from the blood pump. Both versions are equally encompassed by the present invention.

The method according to the present invention encompasses in certain embodiments the step of introducing or entering air into line interior portions of the extracorporeal blood circuit by operating the blood pump. The air may for example be atmospheric air. The present invention is, however, not intended to be limited to the sole use of air, but include all gaseous fluids instead of air which are suitable for the purposes of the present invention.

Introducing air into line interior portions of the extracorporeal blood circuit after termination of the blood treatment session may take place exclusively or in a supporting way by utilization of the blood pump, by utilization of the conveying device or by utilization of the source of compressed air.

Combinations of the before-mentioned options are also encompassed according to the present invention, also passively allowing air to enter.

Introducing substituate liquid into line interior portions of the extracorporeal blood circuit takes place by operating the blood pump and/or the second conveying device.

The blood pump may convey substituate liquid by drawing it from a supply line from a container for the substituate liquid, wherein the supply line enters into the extracorporeal blood circuit between the suction side of the blood pump and a detection device. For this, for example a tube clamp which is provided in the arterial branch of the extracorporeal blood circuit may be provided.

If it is intended that the blood pump introduces and conveys both blood and substituate liquid into the extracorporeal blood circuit, the method according to the present invention may be executed with just one pump. Even though such a further preferred embodiment is encompassed by the present invention, hereafter embodiments are described in which a blood pump and a second conveying device are used. The following description shall simplify the understanding of the principles and functions of the individual components on which the present invention is based.

A "substituate liquid" may be for example any commonly known substituate liquid which is used during a blood treatment such as, e.g., a hemodiafiltration, preferably a solution or isotonic saline solution which has already been used during the blood treatment session which thus was already integrated or introducible into the extracorporeal blood circuit via a fluid connection, such as for example a 0.9% NaCl solution.

With the method according to the present invention, both air and substituate liquid or an arbitrary fluid which is usefully applicable within the scope of the present invention are introduced or inserted into line interior portions of the extracorporeal blood circuit after termination of a blood treatment session. Among other functions, the substituate liquid may hereby preferably rinse line interior portions of the extracorporeal blood circuit in order to prevent a contamination risk.

It may further preferred decrease or prevent foaming, e.g., at the outlet of the blood filter.

Among other functions, the air may preferably displace liquids such as blood from line interior portions of the extracorporeal blood circuit and/or from the blood filter and thus reduce the weight of the blood filter or of the extracorporeal blood circuit to be disposed of.

In a further preferred embodiment according to the present invention, detecting a qualitative change of the content of line interior portions of the extracorporeal blood circuit by utilization of at least one detection device which is arranged in a section of the extracorporeal blood circuit is encompassed.

The qualitative change may relate to one or several areas or sections of the extracorporeal blood circuit, for example an area or section in which the detection device is arranged.

A "qualitative change of the content of line interior portions" includes a change or amendment in the composition of the content of line interior portions of the extracorporeal blood circuit, such as for example a change of the individual parts of blood, substitute liquid and/or air in line interior portions of the extracorporeal blood circuit or a section thereof, in relation to each other. Also the lack of a fluid which was previously present may represent a change in the composition. A qualitative change may also be a transition, e.g., from a gaseous content to a liquid content, or vice versa. This may be for example a transition from blood to air. Likewise, a qualitative change may be a transition from a first liquid content to a second, different liquid content, such as for example a transition from blood to substitute liquid. Such changes may for example be easily detected because of an optical change of the content, such as a brightening or darkening of the content.

The detection device which is arranged in a section of the extracorporeal blood circuit may for example be an optical sensor which detects an optical change of the content of line interior portions of the extracorporeal blood circuit or a property of its content. For example, a blood-air content of line interior portions of the extracorporeal blood circuit is brighter than pure blood because of the oxygen. Further suitable sensors include pressure sensors for detecting a pressure drop when the content in line interior portions of the extracorporeal blood circuit has changed and sensors for detecting a change in the density of the content of line interior portions of the extracorporeal blood circuit, without being limited thereto.

The section of the extracorporeal blood circuit may be an arterial and/or venous section of the extracorporeal blood circuit. The arterial section relates to a section of the extracorporeal blood circuit through which blood flows from the vascular system of the patient in the direction towards the blood treatment device. The venous section relates to the section of the extracorporeal blood circuit through which blood flows from the blood treatment device back to the vascular system of the patient.

The detection device may provide information on the current conditions of a line interior portion at one section of the extracorporeal blood circuit. The method according to the present invention may thus be better and more specifically controllable or regulatable. Furthermore, several detection devices for detecting same parameters in different sections of the extracorporeal blood circuit and/or different detection devices for detecting different parameters in same sections of the extracorporeal blood circuit may also be arranged in it.

In an also preferred refinement of the method according to the present invention, the extracorporeal blood circuit encompasses at least one access device which is connectable with a section of the vascular system of the patient, and the method encompasses disconnecting the extracorporeal blood circuit from the vascular system of the patient, in particular in the area of a first, for example arterial, access device, in particular at an end of the extracorporeal blood circuit.

Disconnecting the extracorporeal blood circuit from the vascular system of the patient means interrupting a connection between the extracorporeal blood circuit and the vascular system of the patient in a section of the extracorporeal blood circuit, for example at an end hereof. In doing so, the interruption may take place both at the arterial and at the venous section, wherein in the present invention disconnecting the arterial section of the extracorporeal blood circuit is preferred.

Disconnecting in the area of the first access device may be understood as for example pulling out the arterial connection needle of a double-needle access.

Disconnecting may also be understood as interrupting the flow connection between the arterial section of the extracorporeal blood circuit and the arterial connection needle.

In the case of the single-needle version, disconnecting may be understood as interrupting the connection between the arterial leg of the Y-shaped section of the extracorporeal blood circuit and the only connection needle which is connected with the vascular system of the patient. The open lumen of the arterial leg of the Y-part may be closed in any manner (manually, mechanically, automatically, and so on) after being separated.

Alternatively or in addition, the same may be applied to the venous section of the extracorporeal blood circuit and the venous access to the vascular system of the patient.

Selecting of the access device with suitable access to the vascular system of the patient is not decisive for the execution of the present invention. To simplify matters, it is frequently referred to the double-needle access here, without having the intention to limit the present invention thereto. It should be borne in mind that the present invention is executable in the same manner with a single-needle access or any further access device which is suitable for the purpose of a blood treatment.

Disconnecting the extracorporeal blood circuit enables in an easy and uncomplicated manner introducing or entering air into line interior portions of the extracorporeal blood circuit for executing the method according to the present invention by utilization of fluid communication with the atmosphere which was established during disconnecting.

A further preferred embodiment of the present invention includes conveying a defined volume of air by utilization of the blood pump.

In order to convey a defined volume of air, the blood pump may for example be operated for a predetermined period of time and/or a certain number of revolutions.

Conveying a defined volume of air may, however, also correspond to conveying a certain feed volume and/or to conveying across a predefined path length across which the content is conveyed along line interior portions of the extracorporeal blood circuit.

A further preferred embodiment of the method according to the present invention encompasses conveying the air-blood content in the line interior portions of the extracorporeal blood circuit until the air-blood content reaches an addition point of the extracorporeal blood circuit for adding substitute liquid into line interior portions of the extracorporeal blood circuit.

The air-blood content may for example be conveyed in a direction away from the disconnected end of the extracorporeal blood circuit.

The air-blood content refers to the content which is created by introducing air into the extracorporeal blood circuit which after the blood treatment session has come to an end already contains blood, wherein blood and air may be the only or substantially the only fluids comprised by the interior of the extracorporeal blood circuit.

An addition point of the extracorporeal blood circuit for substituate liquid into line interior portions of the extracorporeal blood circuit may be arranged in the arterial and/or the venous section of the extracorporeal blood circuit. Preferably, the addition point is arranged in a section of the extracorporeal blood circuit through which the blood flows in a direction away from the disconnected end of the extracorporeal blood circuit. Particularly preferably, the addition point is arranged in the section of the extracorporeal blood circuit through which the blood flows before it reaches and passes the blood treatment device, such as for example a blood filter. Such an addition point may be suitably chosen for adding substituate liquid into the extracorporeal blood circuit such that substituate liquid may be introduced by utilization of the second conveying device as a kind of separating layer or as a kind of separating volume between the blood volume and the air volume.

Suitable examples for an addition point include an opening/closing valve, a stop cock, a connectable branch line of a branched section of the extracorporeal blood circuit and so on.

Conveying the air-blood content may take place by operating the blood pump. When or if the air-blood content or a developing air-blood limit or an air-blood transition area or mixing area reaches the addition point of the extracorporeal blood circuit for adding substituate liquid into the line interior portions of the extracorporeal blood circuit, conveying the air-blood content may be stopped. This may be achieved by stopping the blood pump. Stopping conveying the air-blood content precisely at or by a predefined distance before the addition point for substituate liquid may be achieved by introducing a defined volume of air.

According to the present invention reaching the addition point is preferably and exemplarily to be understood such that the air-blood content is conveyed up to a position close or next to the addition point (orifice, inflow area or the like) for the substituate liquid—for example ahead or in front of it—or exactly up to the addition point for substituate liquid. Reaching is therefore not to be limited to an absolute arriving of the air-blood content at the addition point for substituate liquid. Rather, it is intended to define a relative or otherwise suitable position of the conveyed line interior portions of the extracorporeal blood circuit in relation to the addition point for substituate liquid. This definition applies in its broadest meaning to all embodiments specified herein.

Thus, in a preferred embodiment, the blood pump can be stopped when or if the air-blood boundary has not yet reached the addition point, i.e. before or ahead of it. This may preferably and advantageously take place such that no air is conveyed into a blood filter.

An arrangement in which conveying the substituate liquid starts while the blood pump still draws in air, with the air, however, having not yet reached the addition point for the substituate liquid, is also encompassed by the present invention. This way, flushing the blood filter may advantageously take place.

Besides, a further detection device, such as for example a suitably designed air-blood detector, can be arranged in addition in the section of the extracorporeal circuit, such as for example the arterial section of the extracorporeal blood circuit, for example between the blood pump and the addition point for substituate liquid, and detect the occurrence of air in line interior portion(s) of the extracorporeal blood circuit. Again, such an air-blood detector can be embodied as an optical sensor and detect the occurrence of air in line interior portions of the extracorporeal blood circuit as an optical change of the line content.

When or if the air-blood content reaches the addition point for substituate liquid and/or a detection device detects the occurrence of air in line interior portions of the extracorporeal blood circuit, substituate liquid is entered or introduced into line interior portions of the extracorporeal blood circuit at the addition point for substituate liquid by operating the second conveying device, for example a tube pump or a roller pump.

Conveying substituate liquid may preferably start already before the blood pump draws in air. Alternatively, it can preferably also begin while the blood pump is drawing in air.

The substituate liquid which was entered or introduced into line interior portions of the extracorporeal blood circuit may be an undefined or a predetermined amount or a limited amount of substituate liquid.

Introducing a predefined substituate liquid amount can create an air-substituate liquid-blood content. The term "air-substituate liquid-blood content" hereby indicates that the substituate liquid is introduced between the blood which is conveyed through the extracorporeal blood circuit and the air which is conveyed through the extracorporeal blood circuit and thus creates a kind of buffer between air and blood.

A predetermined substituate liquid amount can correspond to a certain feed volume and/or a certain path length of line interior portions of the extracorporeal blood circuit along which the content is conveyed and can, for example, take place by operating a highly precisely metering membrane pump.

The substituate liquid amount can preferably be predetermined as a magnitude, for example as a volume with a preset value and unit. The absolute magnitude of the substituate liquid amount can preferably be stored and/or insertable for example in a control device of the treatment apparatus according to the present invention. The substituate liquid amount can preferably be exactly conveyed within the frame of the technical precision.

In order to predetermine an exact amount of substituate liquid, e.g., technical specifications of the utilized extracorporeal blood circuit, such as for example the inner volumes of the tube set, can be stored or entered into the control device. By utilization of the technical specifications of the individual components of the extracorporeal blood circuit, for example a required feed time and/or a feed volume can be calculated.

A limited amount of substituate liquid may be for example an amount of substituate liquid which was chosen by utilization of the operating personnel's empirical values. Preferably, a limited amount of substituate liquid can be introduced and conveyed for so long until substituate liquid is detected in line interior portion(s) of the extracorporeal blood circuit at a further detection device. A limited substituate liquid amount thus does not have to be exactly known and/or correspond to a certain feed volume. A limited amount of substituate liquid may, however, be indirectly limited by the inner volume of the components of the extracorporeal blood circuit through which the substituate liquid amount flows, in particular the inner volume of the section between the addition point for substituate liquid and/or the blood treatment device and a further detection device. The volume is hereby thus determined in a limited sense, however, without being exactly known, and without being expressable for example in milliliters and/or without having been stored or being enterable in a controller. Introducing a limited amount of substitute liquid may be of advantage, e.g., if the type of the filter of a blood treatment apparatus or its capacity is unknown or incorrectly stated.

In doing so, the substitute liquid of a storage container provided herefor may be introduced into the extracorporeal blood circuit at the addition point for the substitute liquid via corresponding line systems of the extracorporeal blood circuit.

The air-substitute liquid-blood content which was thus created can be conveyed in the direction away from the disconnected end by operating the blood pump and/or by operating the second conveying device.

Furthermore, after introducing the substitute liquid and thus creating the air-substitute liquid-blood content, air can be further introduced into line interior portions of the extracorporeal blood circuit. This may take place in particular by operating the blood pump and/or by operating the second conveying device. Drawing in and introducing air by utilization of the second conveying device may for example take place by establishing a connection between the suction side of the second conveying device and an exterior of the extracorporeal blood circuit, e.g., the atmosphere.

Further introducing air may serve in particular to substantially exempt line interior portions of the extracorporeal blood circuit from fluids which are present in the interior, in particular blood and substitute liquid, or to reduce the amounts hereof which are present in line interior portions of the extracorporeal blood circuit.

Conveying the air-substitute liquid-blood content may for example be stopped if or when the detection device detects substitute liquid in line interior portion(s) of the extracorporeal blood circuit.

The detection device is defined as above and may be arranged for example in the venous section of the extracorporeal blood circuit, e.g., between the blood treatment device and the venous access device to the vascular system of the patient and in particular between a drip chamber in the venous section and the venous access device.

The detection device may detect the occurrence of substituate liquid in a certain section of line interior portions of the extracorporeal blood circuit, for example by utilization of an optical change of the content of the line interior portions of the extracorporeal blood circuit.

If or when the detection device detects the occurrence of air or substitute liquid in line interior portion(s) of the extracorporeal blood circuit of the extracorporeal blood circuit, conveying the air-substitute liquid-blood content may be stopped.

This may take place by stopping the second conveying device.

Further, in another embodiment of the method according to the present invention it is preferred to arrange the detection device with a predefined distance to a second access device and to convey the content of line interior portions of the extracorporeal blood circuit along the predefined distance to the access device after air was recognized at the detection device.

The second access device may be, without being limited hereto, a venous connection needle of a double-needle access or a venous leg of a Y-piece.

If or when air was recognized by the detection device, the air-substitute liquid-blood content may be conveyed along the predefined distance to the second access device and thus blood and possibly also substitute liquid may be removed from the extracorporeal blood circuit. In doing so, the blood can just be removed from the extracorporeal blood circuit or it may be returned at the same time to the vascular system of the patient.

In some embodiments the methods according to the present invention does not encompass—preferably completely or partly—emptying of the dialysate chamber and/or the dialysate lines over the membrane of the blood filter into the blood chamber of the blood filter.

In a further preferred embodiment of the method according to the present invention, the blood contained in line interior portions of the extracorporeal blood circuit of the extracorporeal blood circuit is returned into the vascular system of the patient—in particular substantially completely—via the second access device. The term "substantially completely returned" means herein that the blood present in line interior portions of the extracorporeal blood circuit is removed nearly without residues from the extracorporeal blood circuit. The blood residues possibly remaining in the extracorporeal blood circuit for technical reasons such as wetting behavior or the blood residues remaining in the drip chamber are hereby to be regarded as negligibly small.

Returning blood into the vascular system of the patient may take place if or when an end of the extracorporeal blood circuit, such as for example the end of the venous section, e.g., the venous connection needle, is connected with the vascular system of the patient. This connection may be maintained or re-established after the end of the blood treatment session.

Besides, it may further be preferred to also remove the substitute liquid, in particular substantially completely, from line interior portions of the extracorporeal blood circuit. This may be achieved by conveying the content of line interior portions of the extracorporeal blood circuit only along the pre-set distance between the detection device and the access device after the detection device has detected air. The pre-set distance may correlate with the defined feed volume of air which was introduced by utilization of the blood pump.

Substantially completely removing the substitute liquid from the line interior portions of the extracorporeal blood circuit may, as described above in relation to the blood contained in the line interior portions of the extracorporeal blood circuit, be regarded as being also almost residue-free.

A complete or nearly complete removal is, however, not required according to the present invention in order to achieve advantages.

After the complete disconnection of the patient (arterial and venous), one of the known (half-)automated methods for more or less complete emptying of the blood tube set could be optionally executed after the blood was returned to the patient. Such methods convey remaining liquid into, e.g., the so-called rinse port of the dialysis machine. The remaining liquid may of course be conveyed in any arbitrary outlet. Such emptying methods may succeed the method according to the present invention or may be part of an embodiment of the same. However, they are not required for executing the present invention.

As the method according to the present invention as described above is executable with the treatment apparatus according to the present invention, it is referred to the respective embodiments as described above in order to avoid repetition.

A development of the treatment apparatus according to the present invention provides the arrangement of at least one detection device for detecting at least one change of the content of line interior portions of the extracorporeal blood circuit or one property of the content in a section of the extracorporeal blood circuit. A property of the content may be a composition, a physical, chemical or biological magnitude, for example a transparency, a pH value and much more suchlike. A suchlike detection device may correspond to the one described above, thus it is referred to its above description in order to avoid repetition. Vice versa, the explanation with regard to the second detection device may undiminishedly also apply to any other detection device which is also disclosed herein.

A treatment apparatus according to the present invention may, without being limited hereto, be suitable to perform hemodialysis, hemofiltration, hemodiafiltration and separation methods.

An advantage which can be achieved according to the present invention is that a contamination risk during further handling or disposing of the blood filter and/or of the extracorporeal blood circuit may be avoided.

Furthermore, the gross waste weight of the blood filter and/or of the extracorporeal blood circuit may be reduced. As a disposal of contaminated disposables such as blood filter and extracorporeal blood circuit is calculated according to weight, costs may thus advantageously be saved.

In certain embodiments according to the present invention, emptying the dialysate chamber may take place without fluid, in particular air, crossing the membrane and getting into contact with the content of the blood circuit which is connected with the patient.

Emptying at least the blood filter may in certain embodiments of the present invention take place without substantial interaction or without any interaction by the user, e.g., the doctor, at least until the blood filter is removed from the treatment apparatus. A side effect is that the error rate is low. In addition, the user has time for other activities during emptying. This contributes to easing the workload and saving time altogether.

The present invention may further advantageously be used for safe removal of blood from the extracorporeal blood circuit for a treatment apparatus for the extracorporeal blood treatment of a patient after the end of a blood treatment session: Since air and substituate liquid are simultaneously present in the form of an air-substituate liquid-blood content in line interior portions of the extracorporeal blood circuit at the end of the blood treatment session, the blood present in line interior portions of the extracorporeal blood circuit can be removed from the extracorporeal blood circuit. This may take place without the risk of introducing air into the body of the patient.

By conveying, in particular volume-defined, amounts of air and substituate liquid, the content of line interior portions of the extracorporeal blood circuit may be conveyed along predefined distances in the extracorporeal blood circuit and thus a substantial removal of liquids (blood and possibly also substituate liquid) from line interior portions of the extracorporeal blood circuit can be ensured. In doing so, only a small amount of substituate liquid is required. This advantageously decreases the costs and the supply efforts for the substituate used.

The amount of substituate liquid which possibly remains in the blood tube set may, for example, correspond to the volume of the venous section of the extracorporeal blood circuit and amount to, for example, only about 30 ml. Thus, decreasing the waste weight of the extracorporeal blood circuit is already advantageously contributed to. The amount of substituate liquid which remains in the blood tube set, and which is negligible regarding its contribution to the total weight of the tube set, may advantageously serve as safety buffer and remain in the blood tube set for this purpose. This way, introduction of air into the blood circuit of the patient can be prevented.

Introducing substituate liquid among or between the air-blood content in line interior portions of the extracorporeal blood circuit may advantageously contribute to preventing the introduction of air into the vascular system of the patient when emptying the extracorporeal blood circuit while it is connected to the patient, and still blood residues can be flushed from line interior portions of the extracorporeal blood circuit of the extracorporeal blood circuit by utilization of the substituate liquid acting as flushing liquid, and thus a contamination risk can be further excluded. The extracorporeal blood circuit may thus be disposed of in a safe way and with little rest total weight or gross waste weight.

Introducing substituate liquid may further contribute to cleaning a blood filter with different inner capillary diameters from blood, which would be technically hardly realizable by only running air through it, due to the lesser pressure drop across the already air-filled capillaries as opposed to the capillaries which are still filled with blood.

Besides, it may also be possible to minimize foaming, for example at the outlet of the blood filter, by using substituate liquid there, i.e. in particular a liquid, and not only a gas (e.g., air) for displacing blood or emptying.

Since the method according to the present invention may be executed directly after a blood treatment session has come to an end, it is simply and easily executable and does not require any technically complex, time- and/or cost-intensive steps.

The method according to the present invention may advantageously be executed with the substituate liquid which is used or present anyway in a blood treatment, such as for example an isotonic saline solution, e.g., a 0.9% NaCl solution. This in turn advantageously contributes to saving costs and time.

Further, the method according to the present invention may enable removal of blood from the arterial section of the extracorporeal blood circuit and in particular from the arterial connection needle and the return of the blood into the vascular system of the patient. The step of retrogradely pushing out the blood present in the arterial connection needle with the aid of, e.g., a syringe which is filled with saline solution may thus advantageously be avoided.

The method according to the present invention may thus offer the advantage of basically completely regaining the blood present in the line interior portions of an extracorporeal blood circuit after that has been used for a blood treatment for the patient.

The approach according to the present invention ensures that no air enters the vascular system of the patient during emptying. Furthermore, no foaming in the area of a blood filter present in the extracorporeal blood circuit can occur with this method, which would hamper emptying the blood from the extracorporeal blood circuit. Still, blood remaining in the extracorporeal blood circuit constitutes a contamination risk.

Another advantage which is achievable in some embodiments according to the present invention is that for the first time a simple and safe method is proposed for notably reducing the remaining weight of both the blood filter and the blood circuit after termination of the blood treatment. According to the present invention it is thus specified how both the blood filter and the blood circuit are emptied, wherein this may take place in some embodiments completely or nearly completely automatically; in any case this may take place with little activity of the medical personnel. This is achieved not least due to the optimized chronology of emptying the dialysate chamber on the one hand and, on the other hand, the remaining sections of the blood filter and the blood circuit which are also emptied in some embodiments according to the present invention.

BRIEF DESCRIPTION OF THE DRAWING

Hereafter, the method according to the present invention is exemplarily described by preferred embodiments with reference to the appended drawing. In the drawing, it applies that.

DETAILED DESCRIPTION

Figure 1:
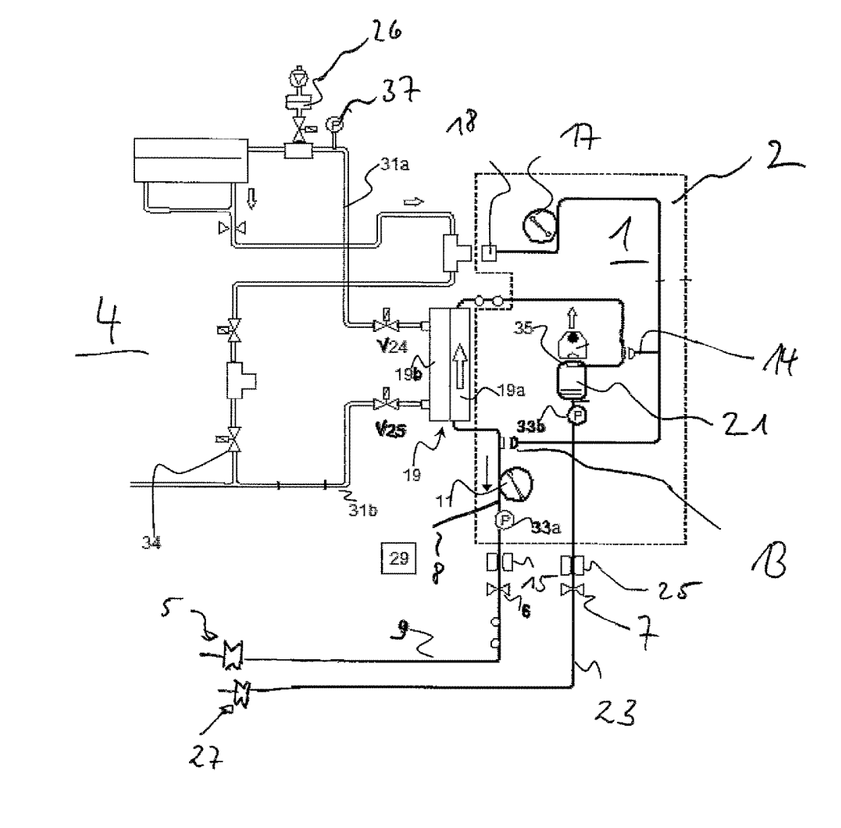
FIG. 1 shows a schematic overview of an exemplary arrangement as a part of a blood cassette for executing the method according to the present invention.

FIG. 1 shows an extracorporeal blood circuit 1 which is connected by utilization of a double-needle access with the vascular system of the patient which is not illustrated here. The blood circuit 1 is present in sections hereof in or on a blood cassette 2. It is connected with a treatment apparatus 4.

The blood circuit 1 comprises an arterial patient tube clamp 6 and an arterial connection needle 5 (as an example for an access device) of an arterial section or an arterial blood line 9. The blood circuit 1 further comprises a venous patient tube clamp 7 and a venous connection needle 27 (as an example for a further or second access device) of a venous section or a venous blood line 23.

A blood pump 11 is provided in the arterial section 9, a substitute pump 17 is connected with a substitute line. The substitute line can be connected with a source of substitute by utilization of an automatic substitute port 18. By utilizing the substitute pump 17, substitute may be introduced via predilution or via postdilution and via associated lines 13 or 14 into line section of the blood circuit 1.

A blood filter 19 is provided in the blood circuit 1. It comprises a blood chamber 19a which is connected with the arterial section 9 and with the venous section 23. A dialysate chamber 19b is connected with a dialysate inlet line 31a which leads to the dialysate chamber 19b and with a dialysate outlet line 31b which leads away from the dialysate chamber 19b.

The dialysate inlet line 31a comprises a valve V24 by which the flow within the dialysate inlet line 31a can be stopped. The dialysate outlet line 31b comprises a valve V25 by which the flow within the dialysate outlet line 31b may be stopped.

The dialysate inlet line 31a is further connected with a source 26 of compressed air via another valve of the apparatus.

For executing the method according to the present invention with the aim of at first emptying the dialysate chamber 19b of the blood filter 19 at the end of the treatment, the dialysate inlet line 31a and the dialysate outlet line 31b each remain connected with the blood filter 19. A negative pressure is applied to the dialysate outlet line 31b via the valve V25. Alternatively or additionally, air is introduced into the dialysate chamber 19b via the machine-internal valve V24. The introduced air may be compressed air from the source 26 of compressed air. The source 26 of compressed air may be a part of the treatment apparatus 4 or be separate from it.

The introduced air may alternatively be atmospheric air which may enter the dialysate inlet line 31a by opening the corresponding valves or other components.

The intake of air or a different gas may be controlled by utilization of one or several sensors, in particular pressure sensors. The one or more sensors may be provided at the dialysate inlet and/or dialysate outlet. In particular, they may be provided in the dialysate inlet line 31a and/or the dialysate outlet line 31b, as is exemplarily shown in FIG. 1 with a pressure sensor 37.

In order to prevent a displacement of dialysate from the dialysate chamber 19b via or across the membrane into the blood chamber 19a, as is intended in certain embodiments according to the present invention, it may be of advantage to keep the blood cassette 2 or the extracorporeal blood circuit 1 closed or to close it against the atmosphere on the blood side. This may be done for example by closing the arterial and venous patient tube clamps 6 and 7 as well as the single-needle valve 34 when using the arrangement illustrated in FIG. 1. Alternatively, a transfer of liquid to the blood side of the membrane may be prevented by suitably choosing the operating pressures. In doing so, the fluid pressure on the blood side of the membrane may be greater or may be set to be higher than on the dialysate side. The pressure on the blood side may be measured for example by means of one or more pressure sensor(s) 33a, b which is/are provided in the extracorporeal blood circuit 1 and in particular in the arterial and/or venous section.

If in addition to this the extracorporeal blood circuit 1 and/or the blood chamber 19a is to be emptied from fluid, i.e. blood, this may be carried out exemplarily as follows:

The extracorporeal blood circuit 1 is being disconnected from the vascular system of the patient by removing the arterial connection needle 5 from the arm of the patient.

For starting the method according to the present invention in a first embodiment, at first the venous patient tube clamp 7 is opened. Subsequently, the blood pump 11 is started and that way air is drawn into the arterial section 9 of the extracorporeal blood circuit 1. The blood pump 11 is exemplarily embodied as a roller pump and introduces an—e.g., predetermined—volume of air into the extracorporeal blood circuit 1 via the disconnected end. After that, the air-blood content is conveyed along line interior portions of the extracorporeal blood circuit 1 in the direction towards the venous connection needle 27 by operating the blood pump 11.

In this embodiment, the predetermined volume of air is defined such that the air-blood limit in line interior portions of the extracorporeal blood circuit 1 comes to a standstill—as exactly as possible—in front of the addition point 13 for substitute liquid. In order to increase the accuracy of stopping the air-blood limit in front of or at the addition point 13 for substitute liquid, an arterial air-blood detector 15 as an example of a detection device may be positioned at a suitable location in the arterial section 9 of the extracorporeal blood circuit 1 between the addition point 13 for substitute liquid and the arterial connection needle 5.

When or if the air-blood limit reaches the addition point 13 for substitute liquid, the blood pump 11 is stopped. The second conveying device, the substitute pump 17 which is here exemplarily embodied as a roller pump, introduces a—preferably—pre-set volume of substitute liquid into line interior portions of the extracorporeal blood circuit 1 via the addition point 13 for substitute liquid. The substitute pump 17 may subsequently be stopped.

Alternatively, the substitute liquid may also be introduced by operating the blood pump 11. For this, the arterial patient tube clamp 6 is closed and the substitute liquid is introduced into the extracorporeal blood circuit 1 via a supply line 8 from a storage container for the substitute liquid.

The achieved air-substitute liquid-blood content is conveyed along line interior portions of the extracorporeal blood circuit 1 by once again operating the blood pump 11 and pressed or conveyed through the blood filter 19, the venous air separation chamber 21 and a venous section 23 of the extracorporeal blood circuit 1 in order to remove the blood from the extracorporeal blood circuit 1 in the direction towards the venous connection needle 27. In doing so, air can in turn be introduced via the blood pump 11 and/or the substitute pump 17.

In the venous section 23 of the extracorporeal blood circuit 1, a venous air-substitute liquid-blood detector 25 is arranged as a further example of a detection device which detects the occurrence of substitute liquid at a predetermined position of line interior portions of the extracorporeal blood circuit 1. The blood pump 11 continues conveying the air-substitute liquid-blood content for so long until the blood in the venous section 23 of the extracorporeal blood circuit 1 is removed from it and returned to the vascular system of the patient via the venous connection needle 27, and/or until air is detected in line interior portions of the extracorporeal blood circuit at the venous air-substitute liquid-blood detector 25. The conveying effort of all pumps is being stopped. An optical and/or acoustical signal can be output.

Controlling or regulating the treatment apparatus 4 may take place by utilization of a control or regulating device 29.

A second embodiment of the present invention basically corresponds to the first embodiment described above, except that the air-substitute liquid-blood content in line interior portions of the extracorporeal blood circuit 1 after the addition of the substitute liquid is not conveyed along line interior portions of the extracorporeal blood circuit 1 by operating the blood pump 11 but by operating the substitute pump 17.

The present invention is not limited to the embodiments as described above, they only serve illustration. Furthermore, the present invention is not limited to emptying the content or parts hereof while a connection with the vascular system still exists.

What is claimed is:

1. A method for displacing dialysate fluid from a dialysate chamber of a blood filter used for a blood treatment of a patient, the method comprising the steps of:
    after the blood treatment of the patient and prior to emptying a blood chamber of the blood filter such that the blood chamber contains full of blood, closing or sealing the blood chamber against atmosphere wherein the blood filter includes a membrane arranged between the blood chamber and the dialysate chamber, wherein the blood chamber is connected with an arterial blood line leading to the blood chamber and with a venous blood line leading away from the blood chamber, and wherein the dialysate chamber is connected with a dialysate inlet line leading to the dialysate chamber and with a dialysate outlet line leading away from the dialysate chamber; and
    while the blood chamber remains closed or sealed against the atmosphere and prevented from emptying, displacing the dialysate fluid from the dialysate chamber by actively or passively introducing air or a liquid into the dialysate inlet line such that the air or liquid enters the dialysate chamber, wherein no fluid from the dialysate chamber transfers across the membrane during the displacing.

2. The method according to claim 1, further comprising the step of:
    regulating or controlling an introduction of the air into the dialysate inlet line while considering pressure measurements from at least one pressure sensor provided in or on the dialysate inlet line or the dialysate outlet line.

3. The method according to claim 1, wherein the closing or sealing the blood chamber comprises closing at least one of an arterial tube clamp along the arterial blood line and a venous tube clamp along the venous blood line.

4. The method according to claim 1, further comprising the step of:
    closing a valve in a blood cassette to further seal the venous blood line from the atmosphere.

5. The method according to claim 1, further comprising the step of:
    setting or prompting a pressure present in the blood chamber to a pressure value which is above a dialysate pressure present in the dialysate chamber.

6. The method according to claim 1, further comprising:
    after the displacing of the dialysate fluid from the dialysate chamber, emptying the blood chamber.

7. The method according to claim 1, wherein emptying the dialysate chamber is finished and then emptying the blood chamber is started.

8. The method according to claim 1, wherein after the displacing of the dialysate fluid from the dialysate chamber, said blood is removed at least one of: (a) from the blood chamber of the blood filter and (b) from an extracorporeal blood circuit which is connected with the blood filter,
    wherein said blood is removed using a blood pump located along the extracorporeal blood circuit, and a second conveying device configured to at least one of:
    (i) introduce a substitute liquid into the extracorporeal blood circuit and (ii) convey a line content within line interior portions of the extracorporeal blood circuit.

9. The method according to claim 8, further comprising the step of:
    recording a qualitative change of the line interior portions of the extracorporeal blood circuit using a detection device arranged along a section of the extracorporeal blood circuit.

10. The method according to claim 1, further comprising the step of:
    disconnecting the arterial blood line and the venous blood line from the patient's vascular system.

11. The method according to claim 8, further comprising conveying, by the blood pump, a defined volume of air into line interior portions of the extracorporeal blood circuit by operating the blood pump.

12. The method according to claim 8, wherein an air-blood content in the line interior portions of the extracorporeal blood circuit is conveyed until an air-blood boundary reaches an addition point of the extracorporeal blood circuit for the substitute liquid into the line interior portions of the extracorporeal blood circuit, and wherein substitute liquid is introduced into the line interior portions of the extracorporeal blood circuit via the addition point when the addition point is reached by the air-blood boundary.

13. The method according to claim 12, wherein a predetermined amount of the substitute liquid is introduced into the line interior portions of the extracorporeal blood circuit by operating the second conveying device.

14. The method according to claim 12, wherein the substitute liquid introduced is conveyed away from a disconnected end of the extracorporeal blood circuit by operating the second conveying device until a detection device detects the substitute liquid in the line interior portions of the extracorporeal blood circuit.

15. The method according to claim 12, wherein air-substitute liquid-blood content is conveyed along the line interior portions of the extracorporeal blood circuit by at least one of operating the blood pump and operating the second conveying device.

16. The method according to claim 12, wherein the second conveying device introduces the substitute liquid into the line interior portions of the extracorporeal blood circuit at a first point of time and the second conveying device introduces air into the line interior portions of the extracorporeal blood circuit at a second point of time which differs from the first point of time.

17. The method according to claim 9, wherein the detection device is arranged with a predetermined distance to a second access device, and wherein the method further comprises the step of:
 conveying a content of the line interior portions of the extracorporeal blood circuit across the predetermined distance to the second access device after the air is identified by the detection device.

18. The method according to claim 17, wherein the blood contained in the line interior portions of the extracorporeal blood circuit is introduced into the patient's vascular system via the second access device.

19. The method according to claim 1, wherein no fluid is transferred across the membrane during the displacing.

20. The method according to claim 1, further comprising:
 establishing a connection outside of the blood chamber between the arterial blood line and the venous blood line.

21. A system for displacing dialysate fluid from a dialysate chamber of a blood filter used for a blood treatment of a patient, said system comprising:
 a control or regulating device configured to control or regulate the execution of a method comprising:
 after the blood treatment of the patient and prior to emptying a blood chamber of the blood filter such that the blood chamber contains full of blood, closing or sealing the blood chamber against atmosphere, wherein the blood filter includes a membrane arranged between the blood chamber and the dialysate chamber, wherein the blood chamber is connected with an arterial blood line leading to the blood chamber and with a venous blood line leading away from the blood chamber, and wherein the dialysate chamber is connected with a dialysate inlet line leading to the dialysate chamber and with a dialysate outlet line leading away from the dialysate chamber; and
 while the blood chamber remains closed or sealed against the atmosphere and prevented from emptying, displacing the dialysate fluid from the dialysate chamber by actively or passively introducing air or a liquid into the dialysate inlet line such that the air or liquid enters the dialysate chamber, wherein no fluid from the dialysate chamber transfers across the membrane during the displacing.

22. The system according to claim 21, further comprising:
 a blood pump arranged along an extracorporeal blood circuit that is connected with the blood filter, the blood pump operable for conveying blood within line interior portions of the extracorporeal blood circuit; and
 a device for introducing air into the dialysate inlet line.

23. The system according to claim 22, further comprising:
 a conveying device for at least one of introducing a substitute liquid into the line interior portions of the extracorporeal blood circuit and conveying a line content within the line interior portions of the extracorporeal blood circuit.

24. The system according to claim 22, further comprising:
 a detection device arranged in or at a section of the extracorporeal blood circuit for detecting a change of a property of the line content within the line interior portions of the extracorporeal blood circuit.

* * * * *

UNITED STATES PATENT AND TRADEMARK OFFICE
CERTIFICATE OF CORRECTION

PATENT NO. : 10,376,628 B2  
APPLICATION NO. : 13/559921  
DATED : August 13, 2019  
INVENTOR(S) : Marco Blasek and Joachim Noack Page 1 of 1

It is certified that error appears in the above-identified patent and that said Letters Patent is hereby corrected as shown below:

On the Title Page

(73) Assignee, Line 1, delete "Fresnius" and insert --Fresenius--.

In the Claims

Column 17, Line 52, Claim 1, after "contains" delete "full of".

Column 19, Line 27, Claim 18, delete "the" and insert --said--.

Column 20, Line 3, Claim 21, after "contains" delete "full of".

Signed and Sealed this  
Twenty-second Day of October, 2019

Andrei Iancu  
*Director of the United States Patent and Trademark Office*